United States Patent [19]
Osaki et al.

[11] Patent Number: 4,781,063
[45] Date of Patent: Nov. 1, 1988

[54] METHOD OF MEASURING ORIENTATION OF SHEET OR WEB LIKE MATERIAL

[76] Inventors: Shigeyoshi Osaki; Shinichi Nagata; Yoshihiko Fujii, all of c/o Kanzaki Paper Manufacturing Co., Ltd., 1-11 Motomachi, Jyokoji, Amagasaki, Hyogo, Japan

[21] Appl. No.: 9,556

[22] Filed: Jan. 30, 1987

Related U.S. Application Data

[63] Continuation of Ser. No. 781,649, Sep. 30, 1985, abandoned.

[30] Foreign Application Priority Data

Oct. 1, 1984 [JP] Japan ................. 59-205992

[51] Int. Cl.$^4$ ............................... G01N 22/00
[52] U.S. Cl. .................... 73/159; 324/58.5 C
[58] Field of Search .......... 73/159; 324/71.1, 58.5 A, 324/58.5 C, 58 C

[56] References Cited

U.S. PATENT DOCUMENTS

| | | | |
|---|---|---|---|
| 2,457,695 | 12/1948 | Liskow | 73/159 |
| 2,548,598 | 4/1951 | Feiker | 324/58.5 C |
| 3,144,601 | 8/1964 | Slabodsky | 73/159 |
| 3,538,434 | 11/1970 | Brown | 324/58.5 A |
| 4,087,746 | 5/1978 | Kanae | 324/58.5 A |
| 4,257,001 | 3/1981 | Partain | 324/58.5 C |
| 4,381,485 | 4/1983 | Steinbrecher | 324/58 C |
| 4,492,915 | 1/1985 | Caspers | 324/58.5 A |
| 4,581,575 | 4/1986 | Osaki et al. | 324/58.5 C X |

FOREIGN PATENT DOCUMENTS

| | | | |
|---|---|---|---|
| 5886443 | 5/1983 | Japan | 324/71.1 |
| 0191658 | 1/1967 | U.S.S.R. | 324/58 C |

OTHER PUBLICATIONS

Tappi Standard T481 SM-60, Suggested Method—1952, Revised—1960, "Fiber Orientation and Squareness of Paper".

Primary Examiner—Daniel M. Yasich
Attorney, Agent, or Firm—Morgan & Finnegan

[57] ABSTRACT

A method of measuring the orientation of the constituents of specimens is disclosed, which includes the steps of preparing a cavity resonator in the form of a pair of waveguides forming a cavity, said waveguides being formed with a slit, inserting a specimen sheet or web in said slit, oscillating said cavity resonator by microwaves of fixed frequency while producing a relative rotation between said inserted specimen sheet or web and the plane of microwaves of the cavity resonator, measuring the amount of attenuation of the output signal or transmitted microwave intensity from said cavity resonator with respect to said exciting input signal, and measuring the orientation from the relation between said amount of attenuation or transmitted microwave intensity and the angle of said specimen sheet with respect to the cavity resonator, said method being characterized in that the oscillation frequency of said microwaves is set shifted slightly toward the higher side from the resonance frequency of the cavity resonator as measured when the specimen sheet or web is inserted in the slit and held therein at an arbitrary angle relative to the cavity resonator.

3 Claims, 2 Drawing Sheets

METHOD OF MEASURING ORIENTATION OF SHEET OR WEB LIKE MATERIAL

This is a continuation of co-pending application Ser. No. 781,649, filed on 9/30/85, now abandoned.

TECHNICAL FIELD

The present invention relates to a method of measuring the orientation of the constituents of sheet-like materials or webs such as paper, plastics, and ceramics or the like in manufacturing process and equipment control thereof.

PRIOR ART

Heretofore, in measuring the orientation of the constituents of a product in sheet or web form, (hereinafter only referred as "sheet"), if the product is a fiber sheet it has been common practice to cut rectangular specimens from the fiber sheet in various directions for tensile strength test for determination of fiber orientation. However, this conventional method, which is a destructive test, entails a great loss of the product itself and takes a substantial time to obtain a test result since the tensile strength test has to be repeated a number of times. Thus, a large amount of reject will be produced from the time a defect is detected till the time the manufacturing process is stopped or readjusted. Moreover, the result of readjustment cannot be found so soon.

PROBLEMS TO BE SOLVED BY THE INVENTION

The present invention is intended to provide a method of measuring the fiber or molecular orientation of paper sheets and the like, which method is non-destructive and capable of continuous measurement and giving a test result in a short time (substantially real time).

SUMMARY OF THE INVENTION

To achieve said object, the invention consists in using microwaves and a device formed with a slit for inserting a specimen into a tubular body forming the cavity of a cavity resonator, oscillating the cavity resonator with a predetermined frequency while producing a relative rotation between the specimen and the plane of microwaves of the cavity resonator, and detecting the corresponding molecular or other orientation from the relation between the amount of attenuation of electric signal output from the resonator and the relative angle of the specimen. More specifically, the invention utilizes a phenomena in which the dielectric loss and resistance loss in the resonator system is at a maximum when the direction of the electric field of microwaves coincides with the direction of the molecular orientation or the like of a sheet.

DESCRIPTION OF THE PREFERRED EMBODIMENTS

Figure 1:
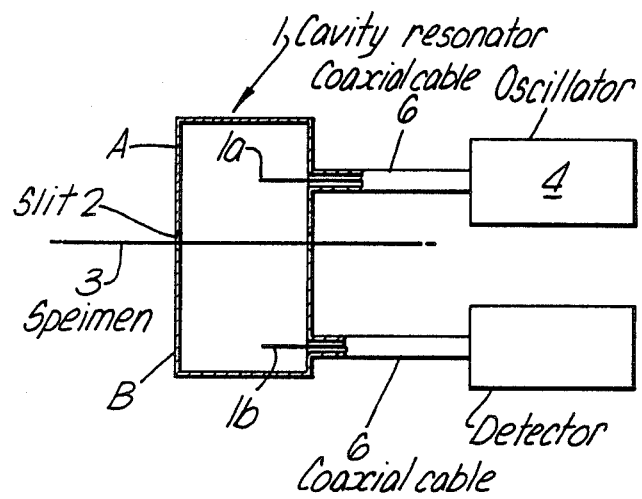
FIG. 1 is a schematic sectional view of an embodiment of the invention.

FIG. 1 shows a method according to an embodiment of the invention applied to a paper manufacturing process. In this figure, the numeral 1 denotes a cavity resonator for which the suitable resonance frequency is in the range of 1 GHz to 30 GHz. The cavity resonator 1 comprises a double head type waveguide bisected into a transmitting section A and a receiving section B by a slit 2 formed in the peripheral wall in the middle where a loop of the electric field is to be formed. The character 1a denotes a transmitting antenna in the transmitting section A and 1b denotes a receiving antenna in the receiving section B. A specimen 3 is inserted in the slit 2 and the cavity resonator 1 is oscillated with microwaves of fixed frequency while rotating either the specimen 3 or the cavity resonator. The numeral 4 denotes a microwave oscillator; 5 denotes a detector; and 6 denotes coaxial cables for connecting the transmitting and receiving antennas 1a and 1b.

Figure 2:
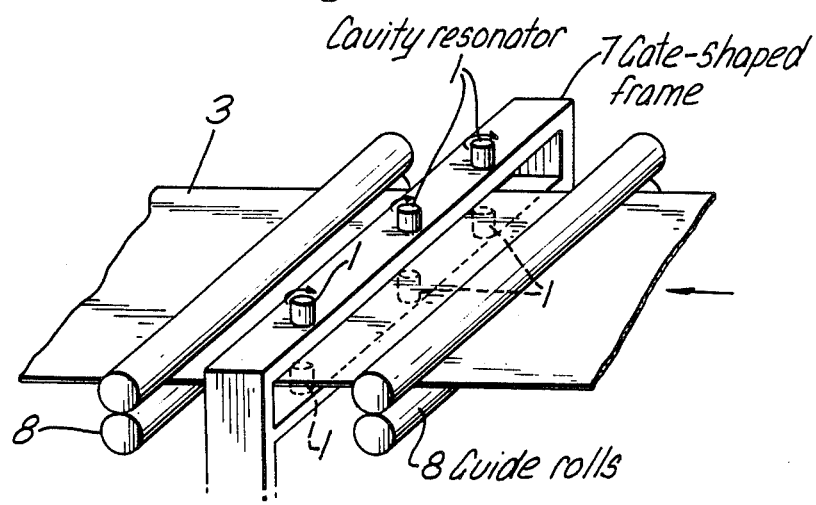
FIG. 2 is a perspective view showing an example of use of said embodiment.

FIG. 2 shows an example in which the invention is applied to a testing device for a paper manufacturing line. A gate-shaped frame 7 through which a band of paper is passed is provided with a plurality (three, in this case) of cavity resonators 1 which are adapted to be synchronically rotated by mechanical means. The numeral 8 denotes paper guide rolls.

Figure 3:
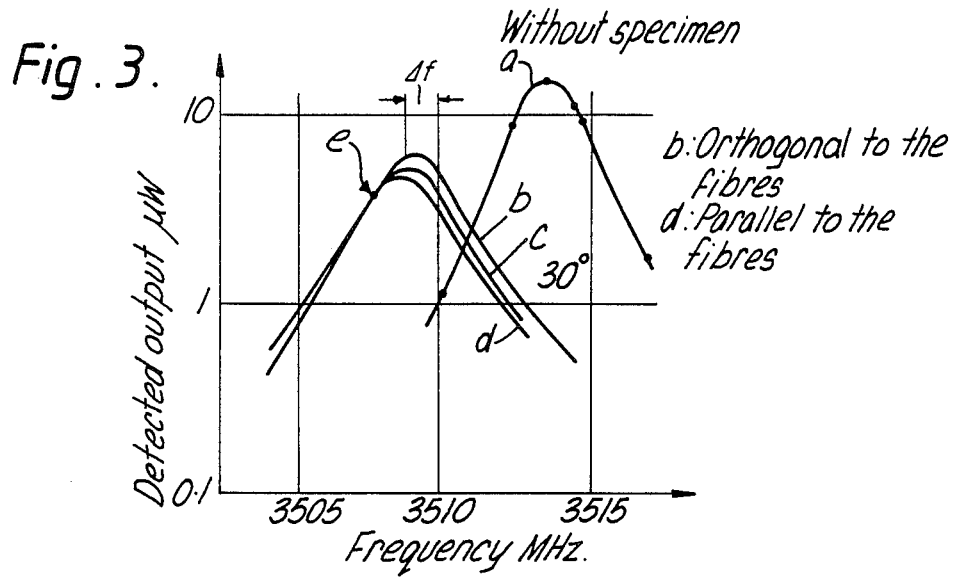
FIG. 3 is a graph showing the function of the invention.

FIG. 3 shows the results of measurement of the detection output from the cavity resonator in the device of FIG. 1, the measurement being made while changing the oscillation frequency, that is, it shows oscillation curves obtained by the cavity resonator. In FIG. 3, a refers to a case where no paper specimen is inserted, the resonance frequency being about 3514 MHz, which is the highest; b refers to a case where a paper specimen is inserted with the electric field at right angles to the fiber orientation; c refers to a case where a paper specimen is inserted with the electric field forming an angle of 30 degrees with the fiber orientation; and d refers to a case where a paper specimen is inserted with the electric field being parallel to the fiber orientation. It is seen from this graph that when the fiber direction is turned through angles between 0 and 90 degrees, both the Q and the resonance frequency of the resonator change with the angle of rotation of the paper. Further, as a result of the Q and the resonance frequency of the resonator changing with the angle of rotation in this manner, it follows that there exists a point where the detection output does not change since the frequency curves intersect each other when the angle of rotation is changed, as shown at point e in FIG. 3. With frequencies around said point e, the orientation of molecules or the like would be difficult. That is, since the decrease in Q and the downward deviation of resonance frequency take place in the same direction, the point e is located on the left-hand side of the hill of the resonance curves. If, therefore, the oscillation frequency for the cavity resonator is set shifted somewhat toward the higher side from the resonance frequency as measured with an arbitrary angle (sheet to resonator), the detection output will be on the right-hand side of or in the vicinity of the peak of each of the curves b, c and e, so that changes in Q dependent on the fiber orientation of paper can be detected with high sensitivity. This resonance frequency is determined by angle-fixed-frequency sweep measurement as an initialization operation with respect to the same specimen. As for the setting range of frequency, detection is possible if the excitation frequency is set in the range of 0 dB to 12 dB down on the right-hand side of the peak, but from the standpoint of accuracy, the range of 0–7 dB is preferable and the range of 1 dB to 3 dB is more preferable.

Figure 4:
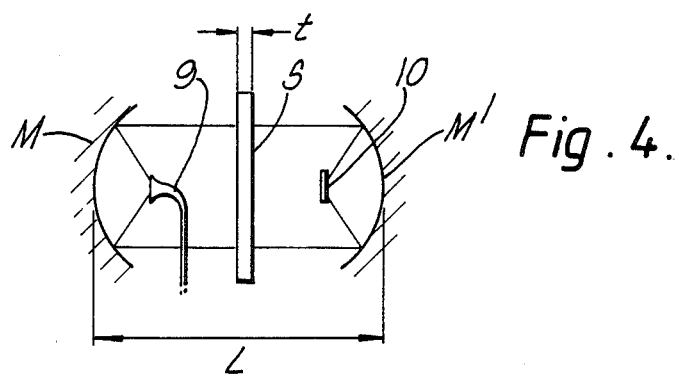
FIG. 4 is a schematic diagram of explaining the principle of the invention.

In the arrangement of the cavity resonator shown in FIG. 4, how the resonance frequency will vary with a sheet S put therein will now be taken up as a general consideration of the above test results. In this figure, M and M' denote parabolic reflectors, with an electromagnetic horn 9 opening to the focus of one paraboloid M and with a reflector 10 located at the focus of the other paraboloid M'. In this arrangement, standing waves with a fixed frequency which is determined by the distance L are produced. Thus, when a sheet S with a specific dielectric constant $\epsilon$ and a thickness t is placed in the middle of the resonator, the effective length L for electromagnetic waves will be increased by $t(\epsilon-1)$ and hence the resonance frequency will be correspondingly decreased.

In FIG. 4, the influence of the sheet S on the sharpness of resonance, or Q will now be considered. To simplify the problem, assume that the physical properties of the sheet are such as to allow the displacement of polarization charge due to electric field and that roughly such displacement tends to occur more readily in the direction of molecules than at right angles thereto. Then, it is expected that the decrease in Q is greater when molecular orientation is parallel to electric field. It seems that the test results of FIG. 3 support this assumption. The interaction between high frequency electromagnetic waves and substance differs with frequency and the causes of this difference are various in terms of atoms, molecules and the gathered state of molecules. Thus, though everything cannot be treated in the same way, the above consideration may be said to be a model consideration close to the fact. It is believed that for frequencies of at least 3 GHz or thereabouts, the results shown in FIG. 3 hold in general as the relation between electric field and direction of molecular orientation. Further, it is seen from said test results that the influence of orientation of sheet-like material leads to a change in Q as well as a change in resonance frequency and that a change in Q is more sharp.

Figure 5:
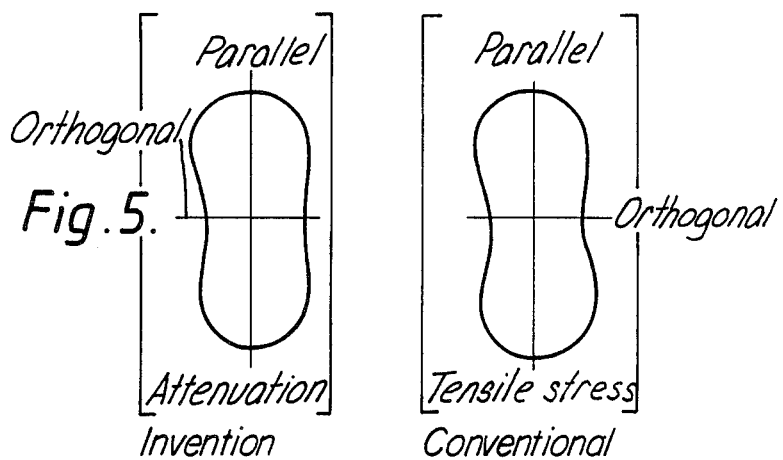
FIG. 5 is a graphic chart for comparison between the present invention and a conventional method.

Therefore, measurement of molecular orientation can be made by detecting a change in Q while fixing the frequency, which means that the circuit arrangement can be simplified much more than when detecting the resonance point by changing the frequency, since it is only necessary to measure a change in detection output. FIG. 5 shows a comparison between the result of measurement of fiber orientation of paper according to the invention and the result of tensile tests using specimens taken from the paper of the same quality, the frequency used fo the former being 3510 MHz; these results will coincide with each other, showing of the usefullness of the invention.

The method of the invention, as described above, comprises the steps of inserting a sample sheet in a small slit defined by bisecting a cavity resonator, oscillating the resonator at substantially the resonance frequency for the resonator as measured after the insertion of the sample, and detecting the orientation from the relation between angle of relative rotation and detection output. Thus, the method of the invention has the advantage of being capable of conducting tests much more easily and quickly than the conventional method which makes it necessary to cut rectangular specimens for tensile tests. In the present method, since it is only necessary to measure detection output, with frequency fixed, the arrangement of the electric circuit, particularly the oscillating circuit is simplified.

It should be noted as for sheets or webs to be measured in accordance with the invention that may include fiber sheets such as paper sheets, plastic sheets such as are made of polyethylene, polyoxymethylene, polyvinyl chloride, polyvinylidene fluoride, polyethylene terephthalate, polyamides, polyimides or copolymers of their and other polymers, ceramic sheets such as are made of alumina, alumina silicate, barium titanate, titanium oxide, silicon carbide, strontium titanate, carbon sheets, carbon fiber-containing plastic sheets, biomembrane sheets, ionic equilibrium membrane sheets, and cellular sheets encapsulating a material such as high molecular liquid crystal, polymer solvent, colloidal solvent, gel materials, or short filament dispersing fluid.

What is claimed is:

1. A method of measuring the orientation of the constituents of specimens of sheet or web like materials, the steps comprising:

preparing a cavity resonator in the form of a pair of waveguides forming a cavity, said waveguides having opposing openings with respect to one another to form a slit;

inserting a specimen sheet or web in said slit;

oscillating said cavity resonator by microwaves of fixed frequency while producing a rotation between said inserted specimen sheet or web and the plane of the microwaves of the cavity resonator;

measuring the amount of attenuation of the output signal or transmitted microwave intensity from said cavity resonator with respect to said exciting input signal, and measuring the orientation from the relation between said amount of attenuation or transmitted microwave intensity and the angle of said specimen sheet with respect to the cavity resonator;

slightly set shifting the oscillation frequency of said microwaves toward the higher side from the resonance frequency corresponding to an attenuation factor of about 0.3–5.5 dB in the output signal of the cavity resonator as measured when the specimen sheet or web is inserted in the slit and held therein at an angle relative to the cavity resonator.

2. A method as set forth in claim 1, wherein an amount by which the oscillation frequency of microwaves is shifted toward the higher frequency side from said resonance frequency corresponds to an attenuation factor of about 0.5–3.5 dB in the output signal from the cavity resonator.

3. A method as set forth in claim 1, wherein a microwave transmitting antenna and a receiving antenna for receiving the transmitted output are respectively installed at said opposing openings of said slit within said waveguide.

* * * * *